US011009453B2

(12) United States Patent
Hanya et al.

(10) Patent No.: US 11,009,453 B2
(45) Date of Patent: May 18, 2021

(54) SPECTRAL CURVE ACQUIRING DEVICE, CONCRETE MEASURING INSTRUMENT, SPECTRAL CURVE ACQUIRING METHOD AND CONCRETE MEASURING METHOD

(71) Applicants: TOPCON CORPORATION, Tokyo (JP); MAEDA CORPORATION, Tokyo (JP)

(72) Inventors: Issei Hanya, Tokyo-to (JP); Shugo Akiyama, Tokyo-to (JP); Ryosuke Tomizawa, Tokyo-to (JP); Naoto Kasori, Tokyo-to (JP); Yoshimitsu Nakajima, Tokyo (JP); Yuji Shirane, Tokyo (JP); Satoshi Suenaga, Tokyo (JP)

(73) Assignee: TOPCON Corporation, Tokyo-to (JP)

( * ) Notice: Subject to any disclaimer, the term of this patent is extended or adjusted under 35 U.S.C. 154(b) by 450 days.

(21) Appl. No.: 16/088,131

(22) PCT Filed: Mar. 24, 2017

(86) PCT No.: PCT/JP2017/013497
§ 371 (c)(1),
(2) Date: Sep. 25, 2018

(87) PCT Pub. No.: WO2017/170975
PCT Pub. Date: Oct. 5, 2017

(65) Prior Publication Data
US 2020/0300753 A1    Sep. 24, 2020

(30) Foreign Application Priority Data

Mar. 31, 2016 (JP) .............................. JP2016-071835

(51) Int. Cl.
*G01J 3/02* (2006.01)
*G01N 21/27* (2006.01)
*G01N 33/38* (2006.01)

(52) U.S. Cl.
CPC ........... *G01N 21/27* (2013.01); *G01N 33/383* (2013.01); *G01N 2201/121* (2013.01)

(58) Field of Classification Search
CPC ................. G01N 21/27; G01N 33/383; G01N 2201/121; G01N 21/274; G01N 21/359;
(Continued)

(56) References Cited

U.S. PATENT DOCUMENTS

2007/0086309 A1 * 4/2007 Yang ........................ G11B 7/24
369/112.01

FOREIGN PATENT DOCUMENTS

JP      9-257577 A    10/1997
JP      2008-14779 A   1/2008

* cited by examiner

*Primary Examiner* — Abdullahi Nur
(74) *Attorney, Agent, or Firm* — Nields, Lemack & Frame, LLC

(57) ABSTRACT

A spectral curve acquiring device comprising: a light receiving optical system (6) for irradiating an irradiating light, a light receiving optical system (8) for dispersing and receiving a reflected irradiating light reflected by an object to be measured (7), a distance meter (4) for measuring a distance to the object to be measured, a storage module (25) for storing a plurality of reference spectral curves prepared based on a light receiving intensity for each wavelength at the time of measuring a white reference plate with different distances, and a control arithmetic module (24), wherein the control arithmetic module obtains a light receiving intensity of the dispersed reflected irradiating light for each wavelength based on the reference spectral curve corresponding to a distance to be measured, corrects a measurement (Continued)

spectral curve prepared based on the light receiving intensity, and prepares a spectral reflectance curve.

10 Claims, 7 Drawing Sheets

(58) Field of Classification Search
CPC ........ G01J 3/00; G01J 3/42; G01J 3/02; G01J 3/28
See application file for complete search history.

F I G. 2
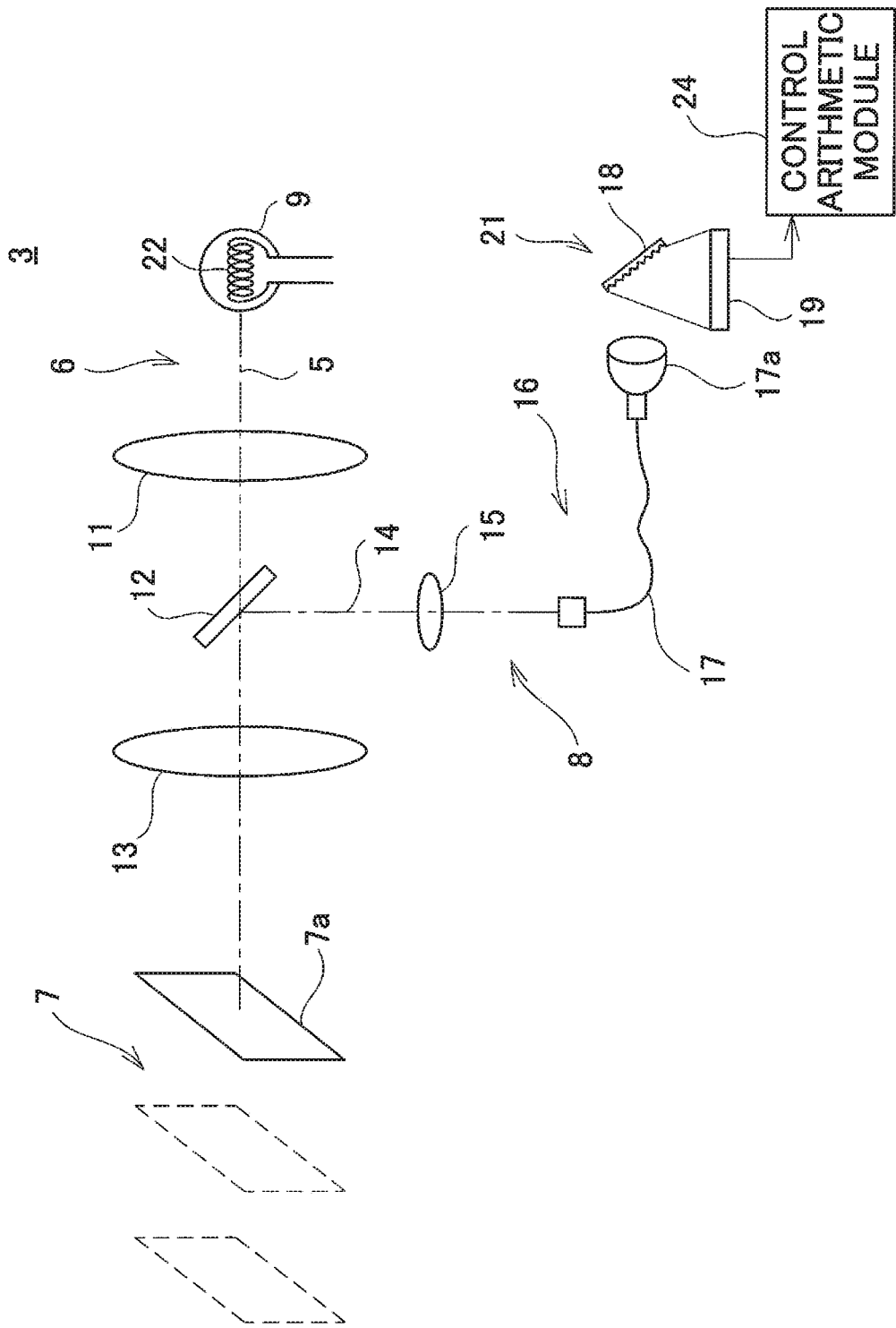

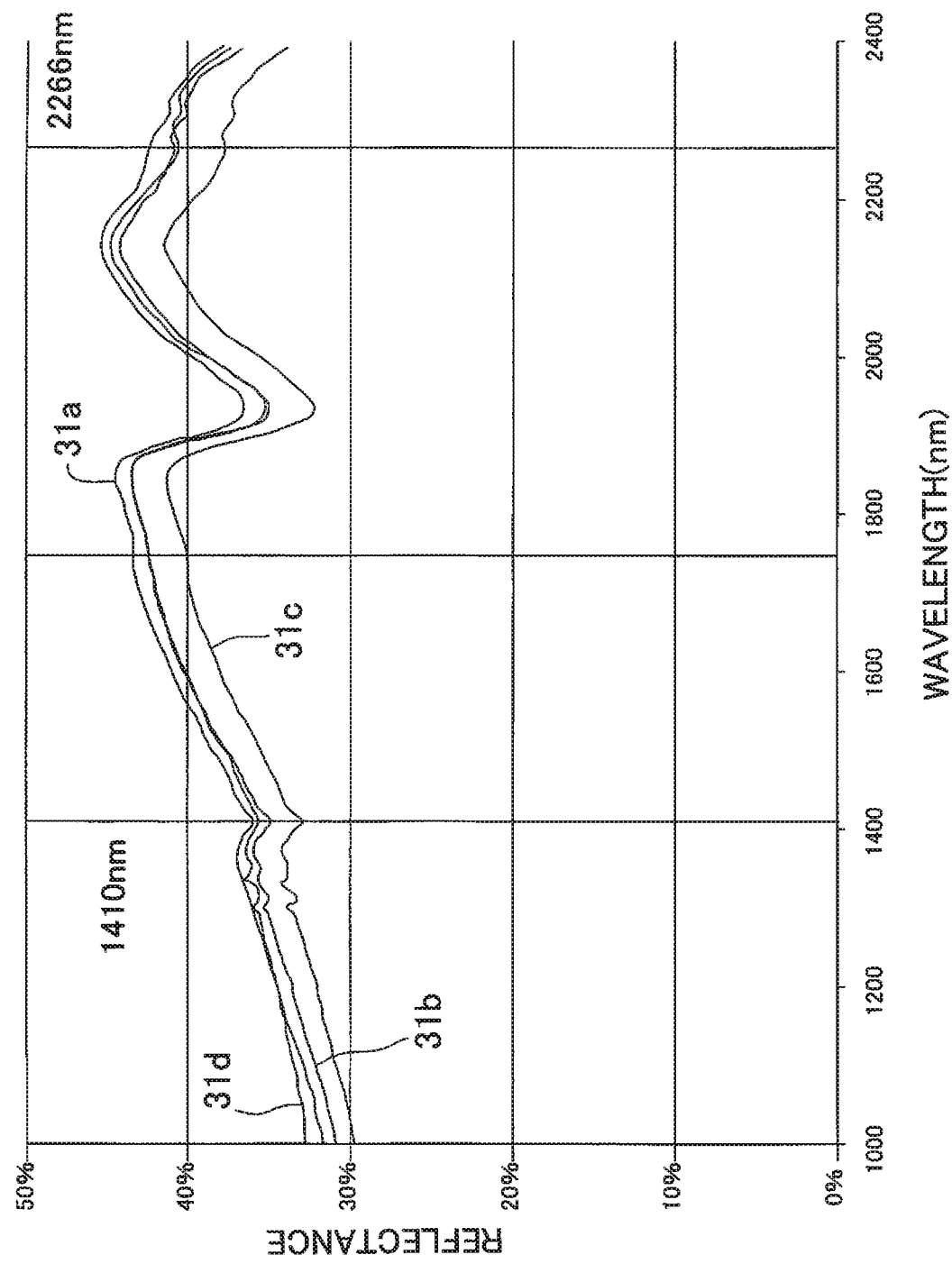

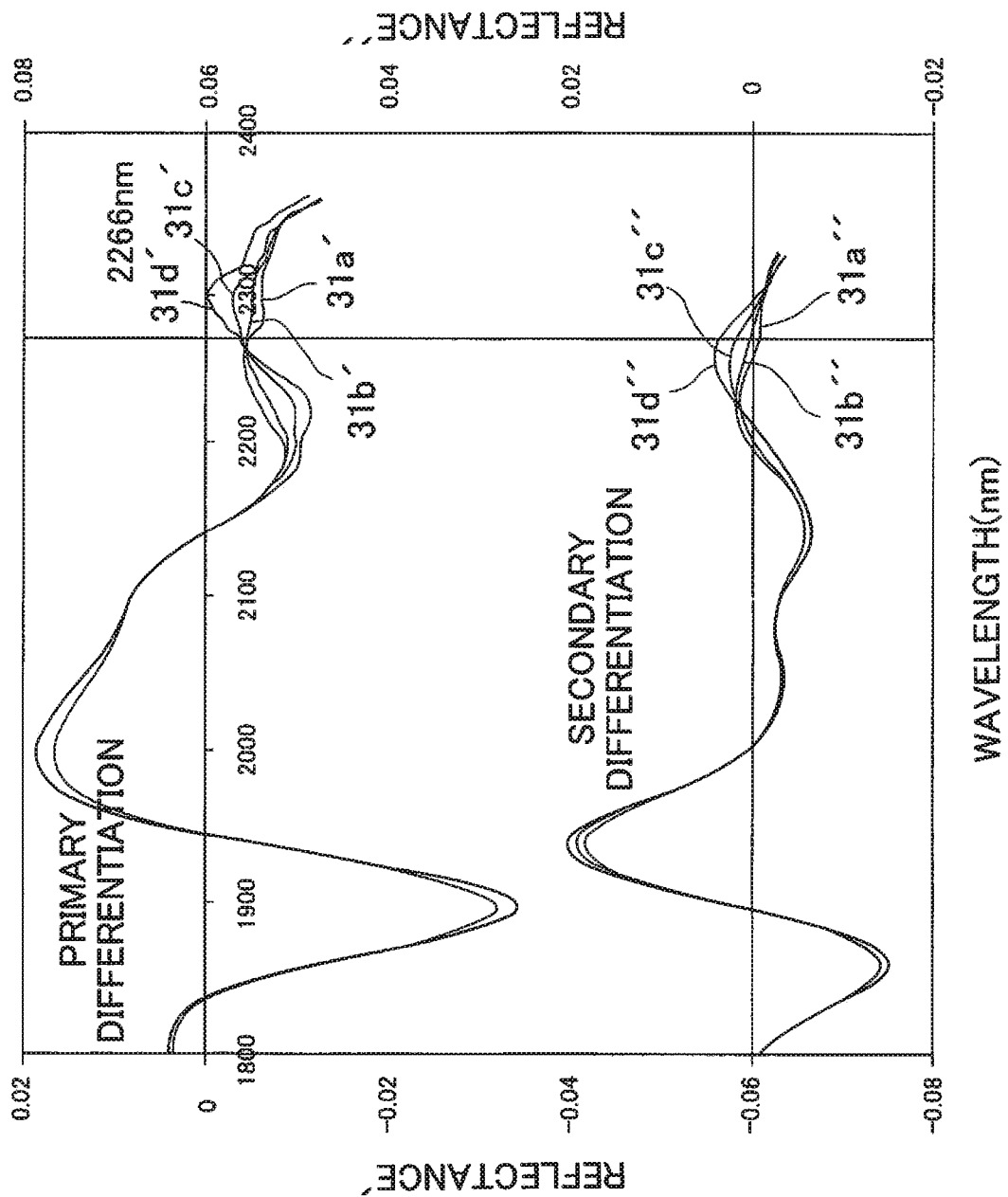

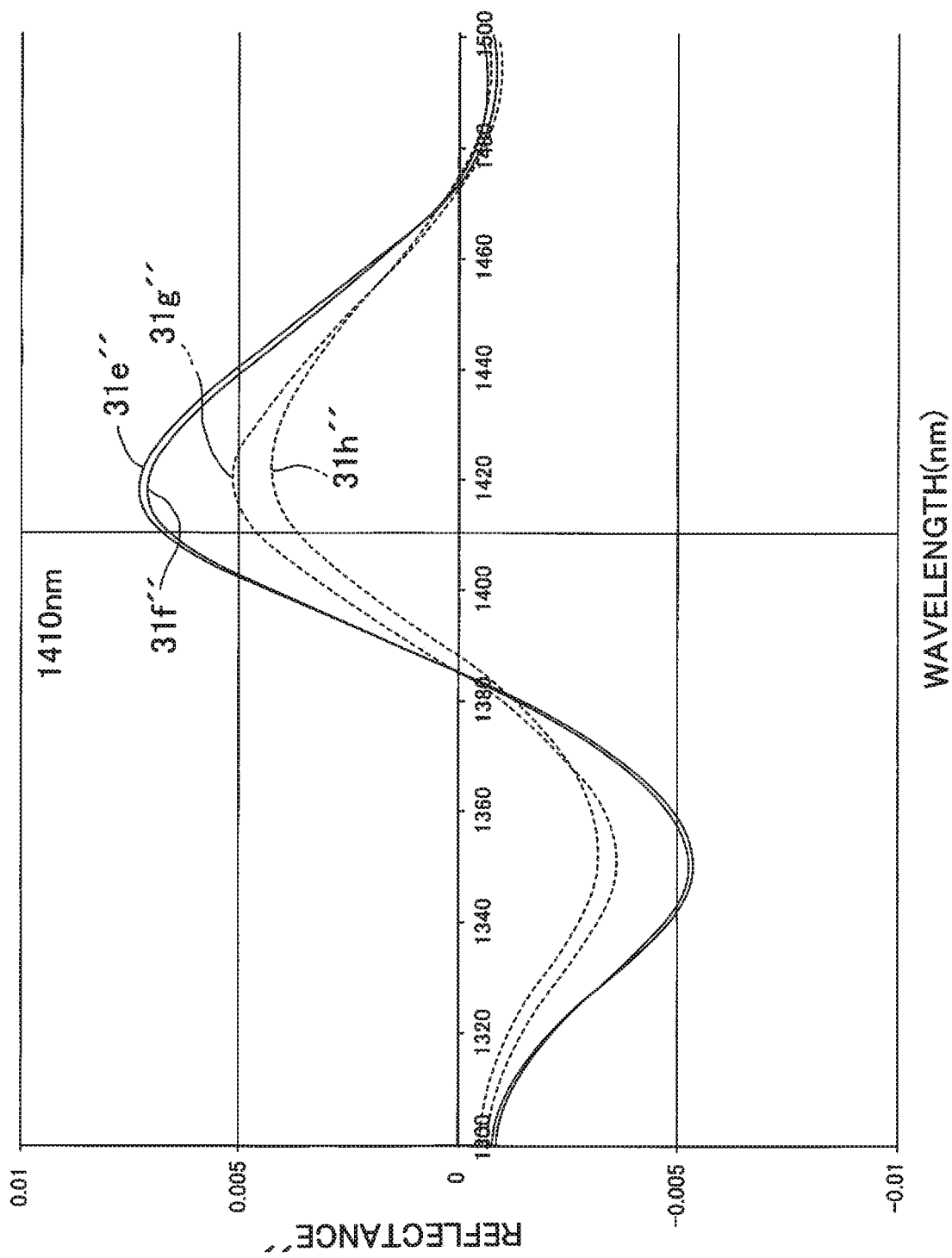

SPECTRAL CURVE ACQUIRING DEVICE, CONCRETE MEASURING INSTRUMENT, SPECTRAL CURVE ACQUIRING METHOD AND CONCRETE MEASURING METHOD

TECHNICAL FIELD

The present invention relates to a spectral curve acquiring device, a concrete measuring instrument, a spectral curve acquiring method and a concrete measuring method by which an information regarding a salt damage and a neutralization of a concrete is acquired in a non-contact and non-destructive manner.

BACKGROUND ART

In an infrastructural structure such as a bridge, a tunnel or the like, a large amount of concrete is used. The concrete deteriorates with time due to, for instance, a salt damage by a splash of a seawater and a diffusion of an anti-freezing agent, a neutralization by carbon dioxide in the air, or the like. Therefore, for a maintenance and an operation of the structure, regularly measuring a salinity concentration in the concrete and a progress of the neutralization and diagnosing a soundness of the concrete has been required in recent years.

Conventionally, in a measurement of an aging deterioration of the concrete, a destructive inspection to cut out a test specimen directly from a structure of an object to be measured, to conduct various types of tests to the test specimen, to measure the salinity concentration, the progress of the neutralization or the like, and to diagnose a degree of a deterioration of the concrete of the object to be measured has been carried out. However, in case of the destructive inspection, since the structure is damaged, it is difficult to repeatedly perform the measurement.

Further, as a method for diagnosing the concrete in a non-destructive manner, there is a non-destructive inspection by which a near-infrared light is irradiated to the concrete, a reflected light from the concrete is spectroscopically measured, and the degree of the deterioration of the concrete is diagnosed.

However, in case of remotely measuring the concrete in the non-contact manner, a waveform shape of a spectrum to be received greatly changes depending on a distance to the concrete. For this reason, in a conventional remote measurement, there was a problem that the salt damage and the neutralization cannot be accurately measured.

It is to be noted that Patent Document 1 discloses a method for diagnosing the concrete by which the reflected light at the time of irradiating near-infrared lights to a concrete surface is spectroscopically analyzed, a concentration of calcium hydroxide is detected from a wavelength region of 900 to 1700 nm, a concentration of chloride ions is detected from a wavelength region of 1700 to 2500 nm using a chemometric method using a PLS regression analysis method, and the deterioration due to the neutralization and the salt damage is diagnosed from the concentration of calcium hydroxide and the concentration of chloride ions. However, Patent Document 1 does not disclose a distance to the concrete surface and a change in the waveform shape of a spectrum depending on a distance.

PRIOR ART REFERENCES

Patent Document

Patent Document 1: Patent Publication JP-A-2008-14779

SUMMARY OF THE INVENTION

Problem to be Solved by the Invention

To solve the problems as described above, it is an object of the present invention to provide a spectral curve acquiring device, a concrete measuring instrument, a spectral curve acquiring method and a concrete measuring method which enable to acquire a spectral curve for acquiring an accurate information related to a salt damage and a neutralization even in a case where a concrete is remotely measured in a non-contact manner.

Means for Solving the Problem

The present invention relates to a spectral curve acquiring device which comprises a light projecting optical system for irradiating an irradiating light, a light receiving optical system for dispersing and receiving a reflected irradiating light reflected by an object to be measured, a distance meter for measuring a distance to the object to be measured, a storage module for storing a plurality of reference spectral curves prepared based on a light receiving intensity for each wavelength at the time of measuring a white reference plate with different distances, and a control arithmetic module, wherein the control arithmetic module obtains a light receiving intensity of the dispersed reflected irradiating light for each wavelength based on the reference spectral curve corresponding to a distance to be measured, corrects a measurement spectral curve prepared based on the light receiving intensity, and prepares a spectral reflectance curve.

Further, the present invention relates to a concrete measuring instrument which comprises a light projecting optical system for irradiating an irradiating light, a light receiving optical system for dispersing and receiving a reflected irradiating light reflected by an object to be measured, a distance meter for measuring a distance to the object to be measured, a storage module for storing a plurality of reference spectral curves prepared based on a light receiving intensity for each wavelength at the time of measuring a white reference plate with different distances, and a control arithmetic module, wherein the control arithmetic module prepares a measurement spectral curve based on a light receiving intensity of the dispersed reflected irradiating light for each wavelength, corrects the measurement spectral curve based on the reference spectral curve corresponding to a distance to be measured and prepares a spectral reflectance curve, and measures an information related to a salt damage and a neutralization of the object to be measured based on a waveform shape of the spectral reflectance curve.

Further, the present invention relates to the concrete measuring instrument, wherein the control arithmetic module calculates a light reception storage time as a correction information from a difference in the light receiving intensity between the measurement spectral curve and the reference spectral curve corresponding to the distance to be measured and corrects the measurement spectral curve based on the correction information, and prepares the spectral reflectance curve.

Further, the present invention relates to the concrete measuring instrument, wherein a plurality of deteriorated spectral reflectance curves which are spectral reflectance curves prepared from test specimens having a known salinity concentration and pH are further stored in the storage module, and the control arithmetic module selects a deteriorated spectral reflectance curve having a waveform shape which coincides with or approximates the spectral reflectance curve from the plurality of deteriorated spectral reflectance curves, and measures the information related to the salt damage and the neutralization of the object to be measured based on the selected deteriorated spectral reflectance curve.

Further, the present invention relates to the concrete measuring instrument, wherein the control arithmetic module measures the information related to the salt damage or the neutralization of the object to be measured by a PLS regression analysis method based on the spectral reflectance curve.

Further, the present invention relates to a spectral curve acquiring method which comprises preparing a plurality of reference spectral curves based on a light receiving intensity for each wavelength at the time of measuring a white reference plate at a plurality of positions with different distances from a light source, respectively, irradiating an irradiating light to an object to be measured, preparing a measurement spectral curve based on a light receiving intensity for each wavelength at the time of dispersing and receiving a reflected irradiating light from the object to be measured, measuring a distance to the object to be measured from the light source, selecting the corresponding reference spectral curve based on a measured distance, correcting the measurement spectral curve based on a correction information acquired from the selected reference spectral curve and the measurement spectral curve, and preparing a spectral reflectance curve.

Further, the present invention relates to a concrete measuring method which comprises irradiating an irradiating light to an object to be measured, and measuring an information related to a salt damage and a neutralization of the object to be measured based on a light receiving result of dispersing and receiving a reflected irradiating light from the object to be measured, and comprises preparing a plurality of reference spectral curves based on a light receiving intensity for each wavelength at the time of measuring a white reference plate at a plurality of positions with different distances from a light source, respectively, preparing a measurement spectral curve based on a light receiving intensity of the light receiving result for each wavelength, measuring a distance to the object to be measured from the light source, selecting the reference spectral curve based on a measured distance, correcting the measurement spectral curve based on a correction information acquired from the selected reference spectral curve and the measurement spectral curve and preparing a spectral reflectance curve, and measuring the information related to the salt damage and the neutralization of the object to be measured based on a waveform shape of the spectral reflectance curve.

Furthermore, the present invention relates to the concrete measuring method which comprises preparing a plurality of deteriorated spectral reflectance curves which are spectral reflectance curves acquired by measuring a plurality of test specimens having a known salinity concentration and pH, selecting a deteriorated spectral reflectance curve corresponding to the spectral reflectance curve from the plurality of deteriorated spectral reflectance curves, and measuring an information related to the salt damage and the neutralization of the object to be measured based on the selected deteriorated spectral reflectance curve.

Effects of the Invention

According to the present invention, the spectral curve acquiring device comprises a light projecting optical system for irradiating an irradiating light, a light receiving optical system for dispersing and receiving a reflected irradiating light reflected by an object to be measured, a distance meter for measuring a distance to the object to be measured, a storage module for storing a plurality of reference spectral curves prepared based on a light receiving intensity for each wavelength at the time of measuring a white reference plate with different distances, and a control arithmetic module, wherein the control arithmetic module obtains a light receiving intensity of the dispersed reflected irradiating light for each wavelength based on the reference spectral curve corresponding to a distance to be measured, corrects a measurement spectral curve prepared based on the light receiving intensity, and prepares a spectral reflectance curve. As a result, the spectral reflectance curve which is required to measure the information regarding the salt damage and the neutralization can be acquired irrespective of a distance to be measured.

Further, according to the present invention, the concrete measuring instrument comprises a light projecting optical system for irradiating an irradiating light, a light receiving optical system for dispersing and receiving a reflected irradiating light reflected by an object to be measured, a distance meter for measuring a distance to the object to be measured, a storage module for storing a plurality of reference spectral curves prepared based on a light receiving intensity for each wavelength at the time of measuring a white reference plate with different distances, and a control arithmetic module, wherein the control arithmetic module prepares a measurement spectral curve based on a light receiving intensity of the dispersed reflected irradiating light for each wavelength, corrects the measurement spectral curve based on the reference spectral curve corresponding to a distance to be measured and prepares a spectral reflectance curve, and measures an information related to a salt damage and a neutralization of the object to be measured based on a waveform shape of the spectral reflectance curve. As a result, an accurate measurement result can be obtained even if a waveform shape of the measurement spectral curve greatly changes due to a change in a distance to the object to be measured, and a stable remote measurement becomes possible.

Further, according to the present invention, the spectral curve acquiring method comprises preparing a plurality of reference spectral curves based on a light receiving intensity for each wavelength at the time of measuring a white reference plate at a plurality of positions with different distances from a light source, respectively, irradiating an irradiating light to an object to be measured, preparing a measurement spectral curve based on a light receiving intensity for each wavelength at the time of dispersing and receiving a reflected irradiating light from the object to be measured, measuring a distance to the object to be measured from the light source, selecting the corresponding reference spectral curve based on a measured distance, correcting the measurement spectral curve based on a correction information acquired from the selected reference spectral curve and the measurement spectral curve, and preparing a spectral reflectance curve. As a result, the spectral reflectance curve which is required to measure the information regarding the salt damage and the neutralization can be acquired irrespective of the distance to be measured.

Furthermore, according to the present invention, the concrete measuring method comprises irradiating an irradiating light to an object to be measured, and measuring an information related to a salt damage and a neutralization of the object to be measured based on a light receiving result of dispersing and receiving a reflected irradiating light from the object to be measured, and comprises preparing a plurality of reference spectral curves based on a light receiving intensity for each wavelength at the time of measuring a white reference plate at a plurality of positions with different distances from a light source, respectively, preparing a measurement spectral curve based on a light receiving intensity of the light receiving result for each wavelength, measuring a distance to the object to be measured from the light source, selecting the reference spectral curve based on a measured distance, correcting the measurement spectral curve based on a correction information acquired from the selected reference spectral curve and the measurement spectral curve and preparing a spectral reflectance curve, and measuring the information related to the salt damage and the neutralization of the object to be measured based on a waveform shape of the spectral reflectance curve. As a result, the accurate measurement result can be obtained even if the waveform shape of the measurement spectral curve greatly changes due to the change in the distance to the object to be measured, and the stable remote measurement becomes possible.

BRIEF DESCRIPTION OF DRAWINGS

FIG. 2 is a drawing to show a light projecting optical system, a light receiving optical system and a spectroscope of the measuring instrument according to the embodiment of the present invention.

FIG. 5 is a graph to show a plurality of spectral reflectance curves with different salinity concentrations.

FIG. 6A is a graph to show primarily-differentiated spectral reflectance curves, and FIG. 6B is a graph to show secondarily-differentiated spectral reflectance curves.

FIG. 7 is a graph in which a plurality of spectral reflectance curves with different pH are secondarily differentiated.

MODE(S) FOR CARRYING OUT THE INVENTION

A description will be given below on embodiments of the present invention by referring to the attached drawings.

Figure 1:
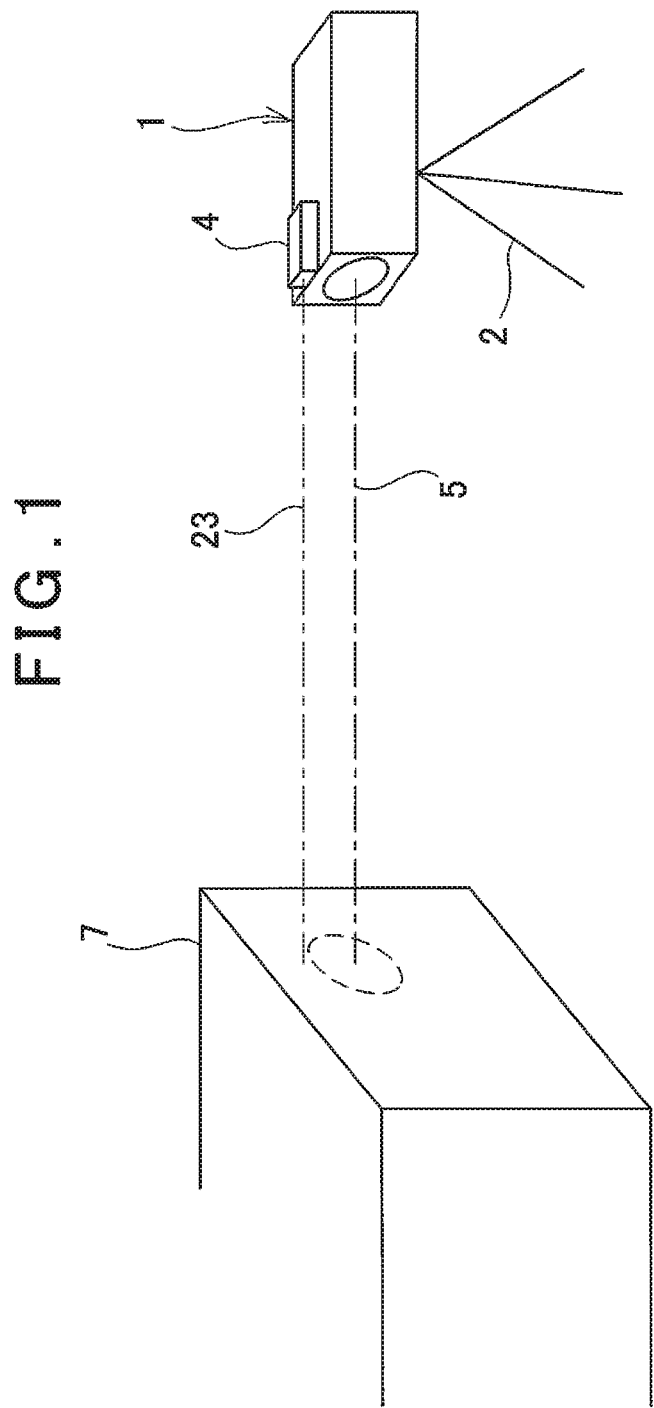
FIG. 1 is a perspective view to show a measuring instrument according to an embodiment of the present invention.

First, in FIG. 1 and FIG. 2, a description will be given on a measuring instrument 1 according to the embodiments of the present invention.

The measuring instrument 1 is installed on a tripod 2. In the measuring instrument 1, a spectrometer 3 is built-in, and on an upper surface of the measuring instrument 1, a distance meter 4 is provided. It is to be noted that the distance meter 4 may be built-in in the measuring instrument 1.

The spectrometer 3 has a light projecting optical system 6 which irradiates an irradiating light including a near-infrared light onto a projection optical axis 5 and has a light receiving optical system 8 which receives a reflected irradiating light from an object to be measured 7, for instance, a concrete structure such a pier portion of a bridge or the like.

The light projecting optical system 6 has the projection optical axis 5, and on the projection optical axis 5, a light source 9, a relay lens 11, a mirror 12 and an objective lens 13 are provided. An irradiating light from the light source 9 is configured to be irradiated to the object to be measured 7 passing through the relay lens 11 and the objective lens 13.

The light receiving optical system 8 has the mirror 12 provided on the projection optical axis 5. Further, the light receiving optical system 8 has an image forming lens 15 provided on a light receiving optical axis 14 branched by the mirror 12 and a light receiving unit 16 provided on an image forming side of the image forming lens 15. The mirror 12 is configured to reflect at least a part of the reflected irradiating light reflected by the object to be measured 7 onto the light receiving optical axis 14.

The light receiving unit 16 has a light receiving fiber 17, a spectroscopic plate 18 and a photodetector 19. One end surface of the light receiving fiber 17 is a light receiving surface, and the light receiving surface is disposed at a focal position of the image forming lens 15. Further, a condenser 17a is provided at an emitting end of the light receiving fiber 17, and a reflected irradiating light from the emitting end is turned to a parallel luminous flux by the condenser 17a and is made to enter the spectroscopic plate 18. Further, a spectrum reflected by the spectroscopic plate 18 is received by the photodetector 19. A light receiving signal from the photodetector 19 is output to a control arithmetic module 24 to be described later. It is to be noted that the spectroscopic plate 18 and the photodetector 19 make up a spectroscope 21.

The light source 9 is, for instance, a halogen lamp which emits the irradiating light including the near-infrared light. By energizing a filament 22, the light source 9 emits, for instance, an irradiating light including a near-infrared light in a wavelength band of approximately 900 nm to 2500 nm in which a state of a deterioration appears.

Further, by emitting a distance measuring light onto a distance measuring optical axis 23 parallel to the projection optical axis 5 and by receiving a reflected distance measuring light reflected by the object to be measured 7, the distance meter 4 is configured to enable to measure a distance to the object to be measured 7. It is to be noted that a distance between the distance measuring optical axis 23 and the projection optical axis 5 is known.

Figure 3:
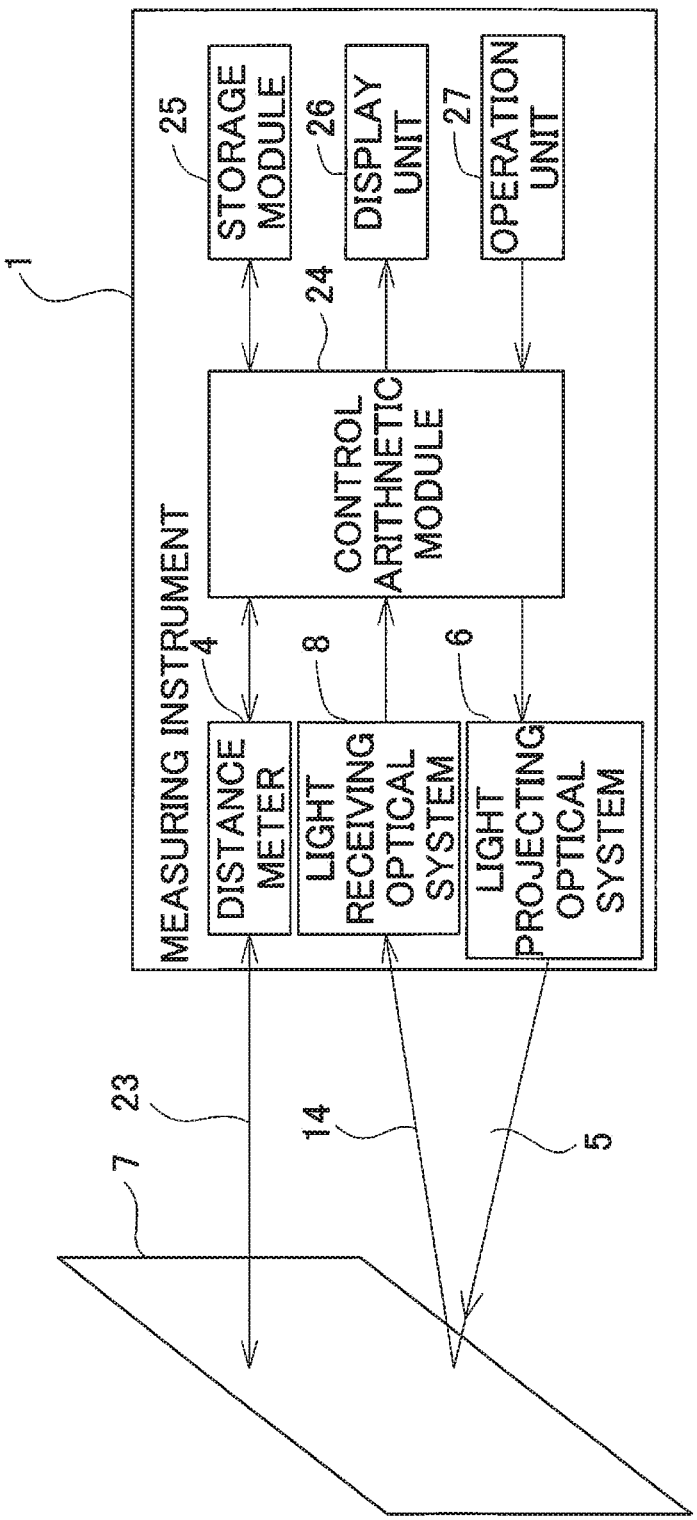
FIG. 3 is a block diagram to show a control system of the measuring instrument according to the embodiment of the present invention.

Next, in FIG. 3, a description will be given on a control system of the measuring instrument 1.

The measuring instrument 1 has the distance meter 4 which measures a distance to the object to be measured 7, the light projecting optical system 6 of the spectrometer 3 which irradiates the irradiating light to the object to be measured 7, the light receiving optical system 8 of the spectrometer 3 which receives the reflected irradiating light from the object to be measured 7, the control arithmetic module 24 such as a CPU or the like, a storage module 25, a display unit 26 and an operation unit 27.

The storage module 25 is, for instance, an HDD or a semiconductor memory or the like. In the storage module 25, programs such as a distance measurement program for making the distance meter 4 measure the distance to the object to be measured 7, a spectroscopic measurement program for acquiring spectroscopic data based on the reflected irradiating light from the object to be measured 7, a spectral curve preparation program for preparing a measurement spectral curve based on a light receiving intensity for each wavelength in the spectroscopic data, a correction program for correcting the prepared measurement spectral curve based on a reference spectral curve (to be described later) corresponding to a measured distance, a spectral reflectance curve preparation program for calculating a reflectance based on the measurement spectral curve and the reference spectral curve and for preparing a spectral reflectance curve, a spectral reflectance curve selection program for comparing a plurality of deteriorated spectral reflectance curves (to be described later) corresponding to the measured distance and a spectral reflectance curve and for selecting a deteriorated spectral reflectance curve having a waveform shape which coincides with or approximates the spectral reflectance curve, and a measurement program for measuring a state of the object to be measured 7 based on the selected deteriorated spectral reflectance curve, and the like are stored.

Further, in the storage module 25, programs such as a deterioration judging program for calculating a salinity concentration or pH based on the prepared spectral reflectance curve, for instance, by a PLS regression analysis and for judging the deterioration, and the like are stored.

Further, in the storage module 25, the prepared measurement spectral curve and spectral reflectance curve, and the like are stored, and data such as the reference spectral curves and the deteriorated spectral reflectance curves which are prepared in advance, and the like are stored.

The display unit 26 is, for instance, a monitor provided in the measuring instrument 1, and displays a measurement result or the like of the object to be measured 7. It is to be noted that the display unit 26 may be an external monitor connected to the measuring instrument 1.

The operation unit 27 is, for instance, a keyboard connected to the measuring instrument 1, and is configured to enable to carry out various types of settings at the time of a measurement. It is to be noted that the display unit 26 may be a touch panel and the display unit 26 may also serve as the operation unit 27.

The reference spectral curve is a spectral curve which is prepared based on the light receiving intensity for each wavelength of when a white reference plate 7a arranged to face the measuring instrument 1 is measured as the object to be measured 7. By changing a distance between the measuring instrument 1 and the white reference plate 7a and by measuring the white reference plate 7a for each distance, a plurality of reference spectral curves corresponding to each of the distances are acquired.

Further, the deteriorated spectral reflectance curve is a spectral reflectance curve of when a concrete of which salinity concentration and pH are known, for instance, of when a test specimen is measured as the object to be measured 7. When a plurality of test specimens with different salinity concentrations and pH are measured while changing a distance between each of the test specimens and the measuring instrument 1, a plurality of deteriorated spectral reflectance curves in which the salinity concentrations and pH are associated with the distances are acquired. It is to be noted that, for a measurement of the salinity concentration and pH, various types of means, for instance, a measurement using the spectroscopic data, a measurement by a destructive inspection of the test specimens, or the like are used.

Next, a description will be given on a measurement of the object to be measured 7 made of concrete using the measuring instrument 1.

First, by the spectrometer 3, the object to be measured 7 is spectroscopically measured. The irradiating light as irradiated onto the projection optical axis 5 by the light source 9 is irradiated to the object to be measured 7 passing through the relay lens 11 and the objective lens 13.

A part of the reflected irradiating light as reflected by the object to be measured 7 is reflected onto the light receiving optical axis 14 by the mirror 12 after passing through the objective lens 13, condensed by the image forming lens 15, and enters the light receiving surface of the light receiving fiber 17.

The reflected irradiating light is turned to a parallel luminous flux by the condenser 17a when being emitted from the light receiving fiber 17, and enters the spectroscopic plate 18. The spectroscopic plate 18 divides and reflects the reflected irradiating light into a plurality of spectrums having a predetermined wavelength and makes the divided spectrums be received by the photodetector 19.

Further, in parallel with a measurement of the spectrometer 3, the distance meter 4 emits the distance measuring light onto the distance measuring optical axis 23, and the reflected distance measuring light from the object to be measured 7 is received by the distance meter 4.

The control arithmetic module 24 calculates a distance to the object to be measured 7 based on a light receiving information of the reflected distance measuring light and acquires the spectroscopic data based on the light receiving information as received by the photodetector 19. The control arithmetic module 24 prepares a measurement spectral curve 29 (see FIG. 4B) from the light receiving intensity for each wavelength based on the spectroscopic data.

Further, the control arithmetic module 24 selects a reference spectral curve 28 (see FIG. 4A) (an information of a change in the reference spectral curve corresponding to the distance to be measured) corresponding to a distance to be measured based on the distance to the object to be measured 7. The control arithmetic module 24 corrects and standardizes the measurement spectral curve 29 based on the reference spectral curve 28 and prepares a spectral reflectance curve 31 (see FIG. 5) (the measurement spectral curve 29 acquired in case of assuming that the measurement is performed by a reference distance to be measured).

The control arithmetic module 24 measures an information regarding a salt damage and a neutralization of the object to be measured 7, that is, a salinity concentration and pH of the object to be measured 7 by a PLS regression analysis method or the like based on a waveform shape of the spectral reflectance curve 31.

Alternatively, the control arithmetic module 24 selects a deteriorated spectral reflectance curve having a waveform shape which coincides with or approximates the spectral reflectance curve 31 from a plurality of deteriorated spectral reflectance curves and measures the information regarding the salt damage and the neutralization of the object to be measured 7, that is, the salinity concentration and pH of the object to be measured 7 based on the selected deteriorated spectral reflectance curve. It is to be noted that, in a case where there are a plurality of approximate deteriorated spectral reflectance curves, an auxiliary deteriorated spectral reflectance curve acquired by averaging the plurality of deteriorated spectral reflectance curves is calculated, and based on the auxiliary deteriorated spectral reflectance curve, the salinity concentration and pH are measured.

A measurement result (a diagnosis result) of the object to be measured 7 is displayed on the display unit 26. It is to be noted that whether or not the spectral reflectance curve 31 is to be compared with the deteriorated spectral reflectance curves is appropriately set according to a purpose of the measurement.

A detailed description will be given below on the measurement of the object to be measured 7.

Figure 4A:
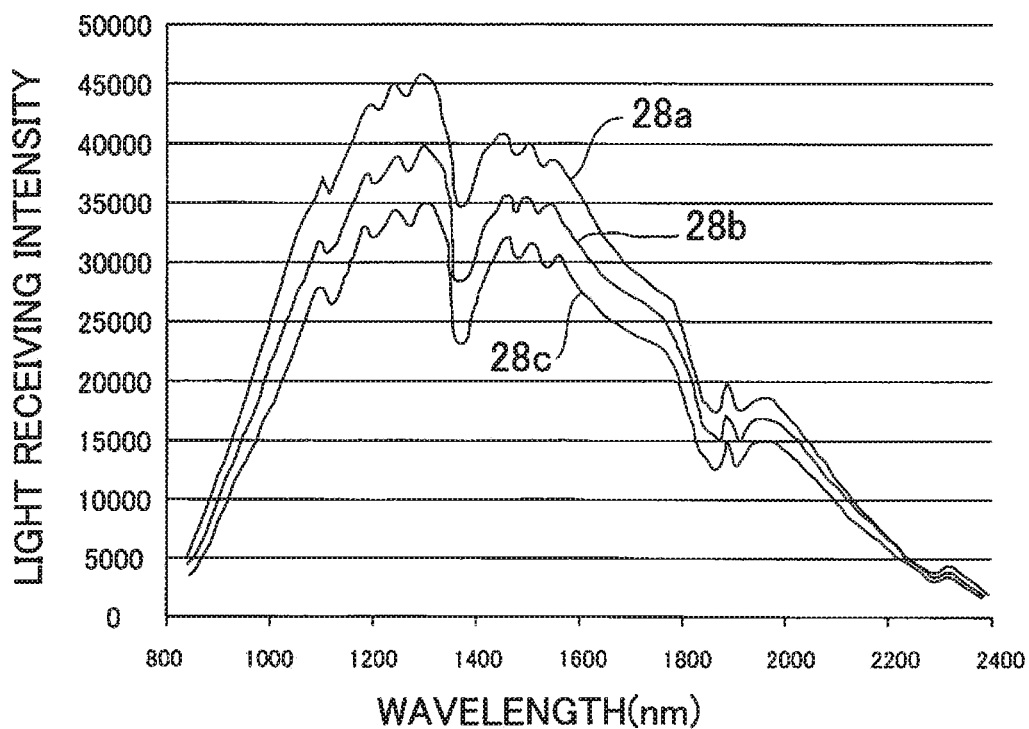
FIG. 4A is a graph to show reference spectral curves.
Figure 4B:
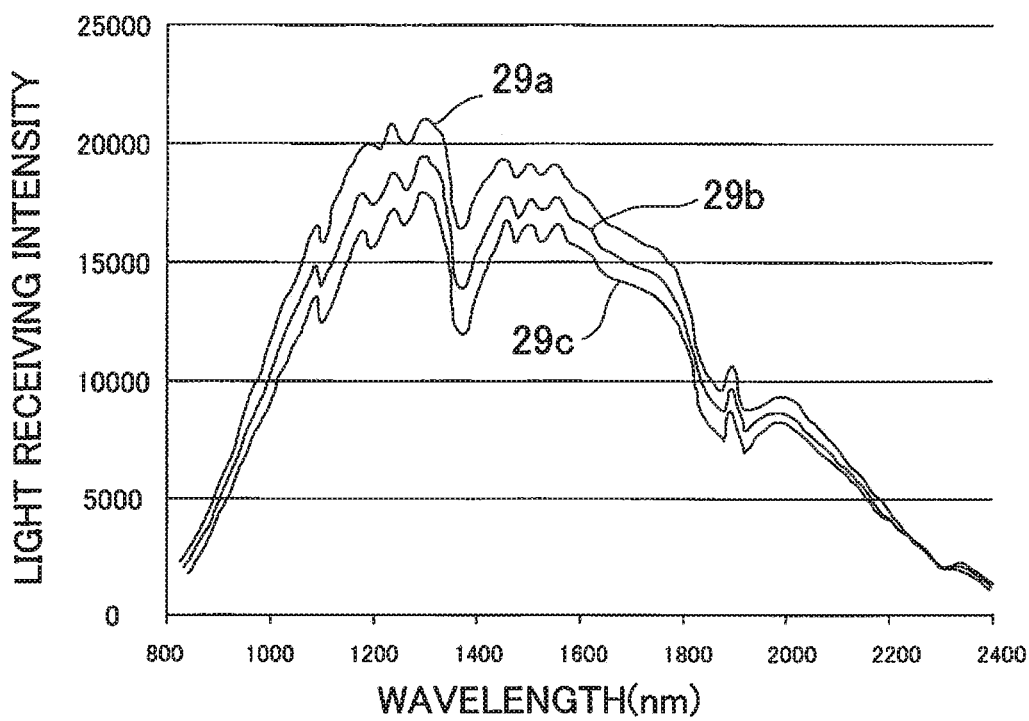
FIG. 4B is a graph to show measurement spectral curves.

FIG. 4A shows reference spectral curves 28a, 28b and 28c acquired in a case where a distance between the measuring instrument 1 and the white reference plate 7a is set to 2 meters, 3 meters and 4 meters, respectively. Further, FIG. 4B shows measurement spectral curves 29a, 29b and 29c acquired in a case where a distance between the measuring instrument 1 and the object to be measured 7 (the concrete) is set to 2 meters, 3 meters and 4 meters, respectively. It is to be noted that, in FIG. 4A and FIG. 4B, a count number of the light receiving intensity of the reflected irradiating light is plotted as an ordinate axis, and a wavelength (nm) is plotted as an abscissa axis. Further, in the following explanation, the reference spectral curves 28a, 28b and 28c are generically referred to as the reference spectral curve 28, and the measurement spectral curves 29a, 29b and 29c are generically referred to as the measurement spectral curve 29.

As shown in FIG. 4A and FIG. 4B, as the distance between the measuring instrument 1 and the object to be measured 7 increases, a light receiving intensity to the measuring instrument 1 decreases, and waveform shapes of the reference spectral curve 28 and the measurement spectral curve 29 change. Further, if the distance between the measuring instrument 1 and the object to be measured 7 remains the same, even though there is a difference in the light receiving intensity, like the reference spectral curve 28a and the measurement spectral curve 29a, shapes of the reference spectral curve 28 and the measurement spectral curve 29 themselves are similar to each other.

Here, when the light receiving intensity decreases and the waveform shapes change, even if, for instance, the object to be measured 7 has the same salinity concentration, a measurement result changes. Therefore, a light reception storage time need to be changed so that the same light receiving intensity can be obtained even if the distance differs. That is, the light reception storage time is set as a correction information, and the measurement spectral curve 29 is corrected based on the set correction information.

When the correction information is set, the reference spectral curve 28 corresponding to the measurement spectral curve 29 is firstly selected. That is, the white reference plate 7a is measured with the same distance as the measurement spectral curve 29, the acquired reference spectral curve 28 is selected, and a difference between the selected reference spectral curve 28 and the measurement spectral curve 29 is calculated.

Based on the calculated difference, the measurement spectral curve 29 is corrected, and the correction information to make the light receiving intensity equivalent to the reference spectral curve 28, that is, a light reception storage time during which the reflected irradiating light is received is calculated.

Further, when the irradiating light is irradiated to the white reference plate 7a, the light receiving intensity of the reflected irradiating light becomes maximum. Therefore, by comparing the light receiving intensity at the time of measuring the white reference plate 7a with the calculated difference, it is possible to calculate a reflectance of the concrete with respect to the white reference plate 7a for each wavelength. By correcting and standardizing the measurement spectral curve 29 based on the reflectance for each wavelength and the correction information, the spectral reflectance curve 31 is prepared from the measurement spectral curve 29.

FIG. 5 shows spectral reflectance curves 31a to 31d of four test specimens of which salinity concentration is known in a case where an ordinate axis represents a reflectance and an abscissa axis represents a wavelength (nm). It is to be noted that the spectral reflectance curve 31a represents a spectral reflectance curve of a test specimen of which chloride ion amount per one cubic meter is 0 kg. The spectral reflectance curve 31b represents a spectral reflectance curve of a test specimen of which chloride ion amount per one cubic meter is 5 kg. The spectral reflectance curve 31c represents a spectral reflectance curve of a test specimen of which chloride ion amount per one cubic meter is 10 kg. The spectral reflectance curve 31d represents a spectral reflectance curve of a test specimen of which chloride ion amount per one cubic meter is 20 kg.

Further, FIG. 6A shows spectral reflectance curves 31a' to 31d' acquired by primarily differentiating the spectral reflectance curves 31a to 31d, and FIG. 6B shows spectral reflectance curves 31a" to 31d" acquired by secondarily differentiating the spectral reflectance curves 31a to 31d.

In the spectral reflectance curves 31a" to 31d" acquired by secondarily differentiating the spectral reflectance curves 31a to 31d, it can be found that the reflectance increases as the salinity concentration rises and a remarkable difference appears in the waveform shape in a wavelength band at about 2260 nm.

Therefore, a measurement of the salinity concentration of the object to be measured 7 can be performed by preparing the spectral reflectance curves 31 and obtaining the reflectance in the wavelength band at about 2260 nm, for instance, at 2266 nm.

Further, FIG. 7 shows spectral reflectance curves 31e" and 31f" (solid lines) acquired by secondarily differentiating spectral reflectance curves 31e and 31f (not shown) of a test specimen A and a test specimen B in which the neutralization does not progress and spectral reflectance curves 31g" and 31h" (broken lines) acquired by secondarily differentiating the spectral reflectance curves 31g and 31h (not shown) of a case where the neutralization progresses in such a manner that the test specimen A and the test specimen B are placed under an environment of high concentration of carbon dioxide.

As shown in FIG. 7, by comparing the spectral reflectance curves 31e" and 31f" with the spectral reflectance curves 31g" and 31h", it can be found that the reflectance in a wavelength band at about 1410 nm decreases as the neutralization progresses.

Therefore, whether or not there is a neutralization of the object to be measured 7 can be measured by preparing the spectral reflectance curves 31 and obtaining the reflectance in the wavelength band at about 1410 nm.

It is to be noted that, in a case where the neutralization progresses, not only the wavelength band at about 1410 nm but also a wavelength band which changes by a change in the salinity concentration is known to change. That is, in a case where the neutralization has progressed, an accurate salinity concentration cannot be measured only by a reflectance in the wavelength band at about 2260 nm.

In the present embodiment, a measurement is performed with respect to a large number of test specimens having known salinity concentration and pH in advance. The prepared spectral reflectance curves 31 of the test specimens are saved and accumulated as deteriorated spectral reflectance curves as associated with a distance to the measuring instrument 1, the salinity concentration and pH, and stored in the storage module 25 by being databased.

At the time of measuring a state of the object to be measured 7, after the spectral reflectance curve 31 of the object to be measured 7 is prepared, a deteriorated spectral reflectance curve which coincides with or approximates the spectral reflectance curve 31 is selected from the accumulated deteriorated spectral reflectance curves. Further, the salinity concentration and pH as associated with the selected deteriorated spectral reflectance curve are output as an information related to the salt damage and the neutralization, that is, the salinity concentration and pH of the object to be measured 7.

Whether or not the spectral reflectance curve 31 coincides with or approximate the deteriorated spectral reflectance curve is judged, for instance, by obtaining a correlation coefficient of two entire curves, or by obtaining a correlation coefficient of a wavelength range as set in advance, or the like.

Further, based on a value of the obtained correlation coefficient, the salinity concentration and pH of the object to be measured 7 may be output as an estimated value.

As described above, in the present embodiment, the light reception storage time of the reflected irradiating light is used as the correction information, and the acquired measurement spectral curve 29 is corrected based on the correction information according to the distance between the measuring instrument 1 and the object to be measured 7.

Therefore, even in a case where the distance between the measuring instrument 1 and the object to be measured 7 changes and the waveform shape of the measurement spectral curve 29 greatly changes, the equivalent spectral reflectance curve 31 can be acquired. That is, irrespective of the distance to be measured, a spectral reflectance curve required for the measurement of the salinity concentration and pH can be acquired. Further, by using the spectral reflectance curve 31, an accurate measurement result can be obtained irrespective of a distance, and a stable remote measurement becomes possible.

Further, the white reference plate 7a is measured a plurality of times with different distances, the plurality of reference spectral curves 28 are prepared in advance and stored in the storage module 25 by being databasing for each distance. Therefore, the measurement of the white reference plate 7a need not to be performed every time the object to be measured 7 is measured, and a workability can be improved.

Further, in the present embodiment, we do not focus on a specific wavelength band in the spectral reflectance curve 31, but we focus on the waveform shape of the entire spectral reflectance curve 31. A deteriorated spectral reflectance curve having a waveform shape which coincides with or approximates a waveform shape of the spectral reflectance curve 31 is selected from the plurality of deteriorated spectral reflectance curves as stored in the storage module 25, and the salinity concentration and pH of the object to be measured 7 is measured based on the selected deteriorated spectral reflectance curve.

Therefore, even in a case where the salt damage and a neutral deterioration occur at the same time and the accurate salinity concentration and pH cannot be measured only by a reflectance in a specific wavelength band, the salinity concentration and pH of the object to be measured 7 can be measured.

It is to be noted that although the accurate salinity concentration and pH cannot be measured only by the spectral reflectance curve 31, many or few of the salinity concentration and a presence or an absence of the neutralization can be judged by the reflectance in the specific wavelength band. Therefore, the spectral reflectance curve 31 need not to be compared with the deteriorated spectral reflectance curves in a case where an accurate measured value is not required, for instance, in a case where only an order of positions to be reinforced is simply determined.

LEGEND OF REFERENCE NUMERALS

1 Measuring instrument
3 Spectrometer
4 Distance meter
6 Light projecting optical system
7 Object to be measured
8 Light receiving optical system
9 Light source
16 Light receiving unit
24 Control arithmetic module
25 Storage module
28 Reference spectral curve
29 Measurement spectral curve
31 Spectral reflectance curve

The invention claimed is:

1. A spectral curve acquiring device comprising: a light projecting optical system for irradiating an irradiating light, a light receiving optical system for dispersing and receiving a reflected irradiating light reflected by an object to be measured, a distance meter for measuring a distance to said object to be measured, a storage module for storing a plurality of reference spectral curves prepared based on a light receiving intensity for each wavelength at the time of measuring a white reference plate with different distances, and a control arithmetic module, wherein said control arithmetic module obtains a light receiving intensity of said dispersed reflected irradiating light for each wavelength based on said reference spectral curve corresponding to a distance to be measured, corrects a measurement spectral curve prepared based on said light receiving intensity, and prepares a spectral reflectance curve.

2. A concrete measuring instrument comprising: a light projecting optical system for irradiating an irradiating light, a light receiving optical system for dispersing and receiving a reflected irradiating light reflected by an object to be measured, a distance meter for measuring a distance to said object to be measured, a storage module for storing a plurality of reference spectral curves prepared based on a light receiving intensity for each wavelength at the time of measuring a white reference plate with different distances, and a control arithmetic module, wherein said control arithmetic module prepares a measurement spectral curve based on a light receiving intensity of said dispersed reflected irradiating light for each wavelength, corrects said measurement spectral curve based on said reference spectral curve corresponding to a distance to be measured and prepares a spectral reflectance curve, and measures an information related to a salt damage and a neutralization of said object to be measured based on a waveform shape of said spectral reflectance curve.

3. The concrete measuring instrument according to claim 2, wherein said control arithmetic module calculates a light reception storage time as a correction information from a difference in the light receiving intensity between said measurement spectral curve and said reference spectral curve corresponding to the distance to be measured and corrects said measurement spectral curve based on said correction information, and prepares said spectral reflectance curve.

4. The concrete measuring instrument according to claim 2, wherein a plurality of deteriorated spectral reflectance curves which are spectral reflectance curves prepared from test specimens having a known salinity concentration and pH are further stored in said storage module, and said control arithmetic module selects a deteriorated spectral reflectance curve having a waveform shape which coincides with or approximates said spectral reflectance curve from said plurality of deteriorated spectral reflectance curves, and measures the information related to the salt damage and the neutralization of said object to be measured based on said selected deteriorated spectral reflectance curve.

5. The concrete measuring instrument according to claim 2, wherein said control arithmetic module measures the information related to the salt damage or the neutralization of said object to be measured by a PLS regression analysis method based on said spectral reflectance curve.

6. A spectral curve acquiring method comprising: preparing a plurality of reference spectral curves based on a light receiving intensity for each wavelength at the time of measuring a white reference plate at a plurality of positions with different distances from a light source, respectively, irradiating an irradiating light to an object to be measured, preparing a measurement spectral curve based on a light receiving intensity for each wavelength at the time of dispersing and receiving a reflected irradiating light from said object to be measured, measuring a distance to said object to be measured from said light source, selecting said corresponding reference spectral curve based on a measured distance, correcting said measurement spectral curve based on a correction information acquired from said selected reference spectral curve and said measurement spectral curve, and preparing a spectral reflectance curve.

7. A concrete measuring method comprising: irradiating an irradiating light to an object to be measured, and measuring an information related to a salt damage and a neutralization of said object to be measured based on a light receiving result of dispersing and receiving a reflected irradiating light from said object to be measured, and comprising: preparing a plurality of reference spectral curves based on a light receiving intensity for each wavelength at the time of measuring a white reference plate at a plurality of positions with different distances from a light source, respectively, preparing a measurement spectral curve based on a light receiving intensity of said light receiving result for each wavelength, measuring a distance to said object to be measured from said light source, selecting said reference spectral curve based on a measured distance, correcting said measurement spectral curve based on a correction information acquired from said selected reference spectral curve and said measurement spectral curve and preparing a spectral reflectance curve, and measuring the information related to the salt damage and the neutralization of said object to be measured based on a waveform shape of said spectral reflectance curve.

8. The concrete measuring method according to claim 7 comprising: preparing a plurality of deteriorated spectral reflectance curves which are spectral reflectance curves acquired by measuring a plurality of test specimens having a known salinity concentration and pH, selecting a deteriorated spectral reflectance curve corresponding to said spectral reflectance curve from said plurality of deteriorated spectral reflectance curves, and measuring an information related to the salt damage and the neutralization of said object to be measured based on said selected deteriorated spectral reflectance curve.

9. The concrete measuring instrument according to claim 3, wherein a plurality of deteriorated spectral reflectance curves which are spectral reflectance curves prepared from test specimens having a known salinity concentration and pH are further stored in said storage module, and said control arithmetic module selects a deteriorated spectral reflectance curve having a waveform shape which coincides with or approximates said spectral reflectance curve from said plurality of deteriorated spectral reflectance curves, and measures the information related to the salt damage and the neutralization of said object to be measured based on said selected deteriorated spectral reflectance curve.

10. The concrete measuring instrument according to claim 3, wherein said control arithmetic module measures the information related to the salt damage or the neutralization of said object to be measured by a PLS regression analysis method based on said spectral reflectance curve.

* * * * *